United States Patent
Victors et al.

(10) Patent No.: US 12,300,360 B2
(45) Date of Patent: *May 13, 2025

(54) PREEMPTIBLE-BASED SCAFFOLD HOPPING

(71) Applicant: Recursion Pharmaceuticals, Inc., Salt Lake City, UT (US)

(72) Inventors: Mason L. Victors, Riverton, UT (US); Nathan C. Wilkinson, Salt Lake City, UT (US); Scott Nielsen, Salt Lake City, UT (US); Jorge Aguilera-Iparraguirre, Jamaica Plain, MA (US)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/665,445

(22) Filed: May 15, 2024

(65) Prior Publication Data
US 2024/0304286 A1 Sep. 12, 2024

Related U.S. Application Data

(63) Continuation of application No. 18/222,302, filed on Jul. 14, 2023, now Pat. No. 12,014,804, which is a
(Continued)

(51) Int. Cl.
*G06F 3/00* (2006.01)
*G06F 9/48* (2006.01)
(Continued)

(52) U.S. Cl.
CPC ........... *G16C 20/40* (2019.02); *G06F 9/4881* (2013.01); *G06F 9/54* (2013.01); *G06F 11/0715* (2013.01)

(58) Field of Classification Search
CPC ........................................ G06F 9/48
See application file for complete search history.

(56) References Cited

U.S. PATENT DOCUMENTS

| 6,212,649 | B1 | 4/2001 | Yalowitz et al. |
| 6,941,229 | B1 * | 9/2005 | Elleman ................. A61P 43/00 |
| | | | 702/19 |

(Continued)

FOREIGN PATENT DOCUMENTS

| JP | 2823520 B2 | 11/1998 |
| KR | 102240825 B1 | 4/2021 |

(Continued)

OTHER PUBLICATIONS

Isaac H. Kim, Fault-tolerant resource estimate for quantum chemical simulations: Case study on Li-ion battery electrolyte molecules (Year: 2021).*

(Continued)

*Primary Examiner* — Lechi Truong

(57) ABSTRACT

In a method of molecular scaffold hopping an interface of a scheduler computer sends instructions, prepared by the scheduler computer, to a job runner computer to perform a plurality of separate computational tasks. Each of the separate computational tasks includes calculating one or more chemical properties for a query molecule or molecules in a library of molecules. One or more of the plurality of separate computational tasks performed on the job runner computer are preemptible computing instances. Status indicators sent from the job runner computer are received by the interface for each of the plurality of separate computational tasks. The indicators are one of: incomplete, completed, or failed computing instances. The interface resends the instructions to the job runner computer that correspond to the separate computational tasks having the failed computing instance (Continued)

indicator to increase fault-tolerance against the separate computational tasks not attaining the completed computing instance indicator.

19 Claims, 3 Drawing Sheets

Related U.S. Application Data continuation of application No. 18/054,567, filed on Nov. 11, 2022, now Pat. No. 11,705,223, which is a continuation of application No. 16/933,225, filed on Jul. 20, 2020, now Pat. No. 11,501,853.

(51) Int. Cl.
*G06F 9/54* (2006.01)
*G06F 11/07* (2006.01)
*G16C 20/40* (2019.01)

(56) References Cited

U.S. PATENT DOCUMENTS

| | | | |
|---|---|---|---|
| 8,024,127 B2 | 9/2011 | Zemla | |
| 8,935,375 B2 | 1/2015 | Dournov et al. | |
| 10,628,219 B2 | 4/2020 | Joseph | |
| 11,501,853 B2 | 11/2022 | Victors et al. | |
| 11,705,223 B2 | 7/2023 | Victors et al. | |
| 2003/0143580 A1* | 7/2003 | Straus | G01N 33/56938 435/6.1 |
| 2003/0167128 A1 | 9/2003 | Cramer et al. | |
| 2004/0254735 A1 | 12/2004 | Horn et al. | |
| 2006/0225075 A1* | 10/2006 | Mankovski | G06F 9/5027 718/102 |
| 2007/0088979 A1 | 4/2007 | Pomaranski et al. | |
| 2007/0294697 A1* | 12/2007 | Theimer | G06F 9/5027 718/102 |
| 2009/0234589 A1 | 9/2009 | Eberhart et al. | |
| 2013/0047034 A1 | 2/2013 | Salomon et al. | |
| 2015/0143381 A1 | 5/2015 | Chin et al. | |
| 2016/0170811 A1 | 6/2016 | Peacock et al. | |
| 2017/0220433 A1 | 8/2017 | Dimnaku et al. | |
| 2018/0011899 A1 | 1/2018 | Dean et al. | |
| 2022/0020453 A1 | 1/2022 | Victors et al. | |
| 2022/0059195 A1 | 2/2022 | Blevins et al. | |
| 2023/0077085 A1 | 3/2023 | Victors et al. | |
| 2023/0360741 A1 | 11/2023 | Victors et al. | |

FOREIGN PATENT DOCUMENTS

| | | | |
|---|---|---|---|
| SG | 144760 A1 | 8/2008 | |
| WO | WO-9962955 A1 * | 12/1999 | C07K 14/71 |
| WO | 03048340 A2 | 6/2003 | |
| WO | 2007146436 A2 | 12/2007 | |
| WO | 2022020061 A1 | 1/2022 | |

OTHER PUBLICATIONS

PCT/US21/39136, International Search Report and Written Opinion, Mailed Sep. 29, 2021, 6 pgs.
Shubhakankshi Gautam, Preemptable Priority Based Dynamic Resource Allocation in Cloud Computing with Fault Tolerance. (Year:2015) 9 pgs., 2015.
"Preemptible VM instances"; Compute Engine Documentation; https://cloud.google.com/compute/docs/instances/preemptible;, Apr. 20, 2020, 5 pgs.
Laksh; "A practical Introduction to the Use of Molecular Fingerprints in Drug Discovery", https://towardsdatascience-com/a-practical-introduction-to-the-use-of-molecular-fingerprints-in-drug-discovery-7f1502b32b1, Jul. 2, 2019, 5 pgs.
Kinitsky, Digital Computer Calculation of Internal Fault Currents in a Synchronous Machine (Year: 1968).
Zhao, et al., "Preemptive Scheduling Under Time and Resource Constraints", IEEE Transactions on Computers, vol. C-36, No. 8, Aug. 1987, 12 pgs.

* cited by examiner

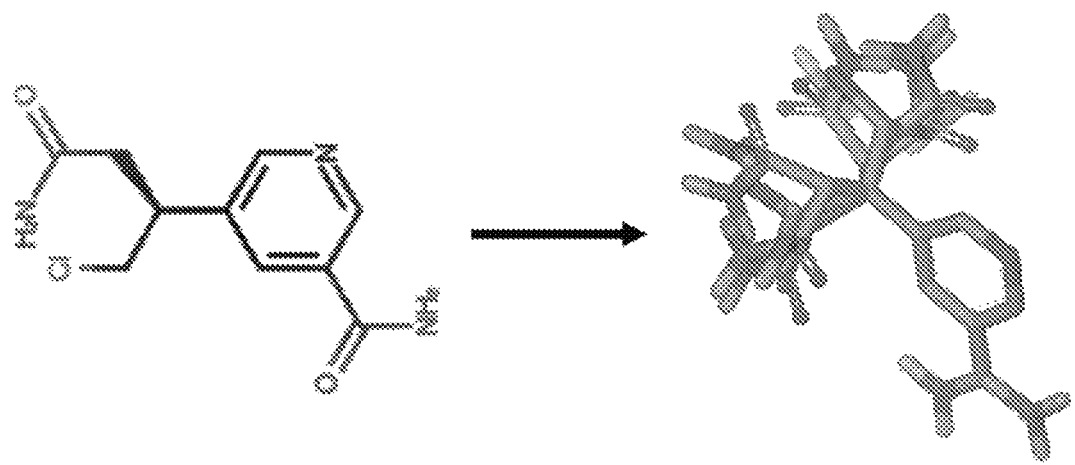
FIG. 3A  2D Structure
FIG. 3B  3D Conformer Ensemble

PREEMPTIBLE-BASED SCAFFOLD HOPPING

REFERENCE TO RELATED APPLICATIONS

This application is a continuation application of and claims priority to and benefit of U.S. patent application Ser. No. 18/222,302 (now issued U.S. Pat. No. 12/222,302) filed on Jul. 14, 2023 entitled "PREEMPTIBLE-BASED SCAFFOLD HOPPING" by Mason Victors et al., and assigned to the assignee of the present application, the disclosure of which is hereby incorporated herein by reference in its entirety.

U.S. patent application Ser. No. 18/222,302 is a continuation application of and claims priority to and benefit of then U.S. patent application Ser. No. 18/054,567 (now issued U.S. Pat. No. 11,705,223) filed on Nov. 11, 2022 entitled "PREEMPTIBLE-BASED SCAFFOLD HOPPING" by Mason Victors et al., and assigned to the assignee of the present application, the disclosure of which is hereby incorporated herein by reference in its entirety.

U.S. patent application Ser. No. 18/054,567 is a continuation application of and claims priority to and benefit of U.S. patent application Ser. No. 16/933,225 (now issued U.S. Pat. No. 11,501,853) filed on Jul. 20, 2020 entitled "PREEMPTIBLE-BASED SCAFFOLD HOPPING" by Mason Victors et al., and assigned to the assignee of the present application, the disclosure of which is hereby incorporated herein by reference in its entirety.

TECHNICAL FIELD

The present disclosure related to a method and apparatus for molecular scaffold hopping in a preemptible computing environment.

BACKGROUND

Molecular scaffold hopping, the switching from one chemical core structure of a molecule to another molecule having a different chemical core structure, as facilitated by computer-aid searching, is widely known and used for drug discovery and medicinal chemistry. Often, molecular scaffold hopping involves starting from some small molecule and finding other small molecules that have similar electrostatic and shape properties. The effort to find such molecules can be highly computing-intensive and therefore both time and financially expensive endeavors.

BRIEF DESCRIPTION

Reference is now made to the following descriptions taken in conjunction with the accompanying drawings, in which.

Figure 1:
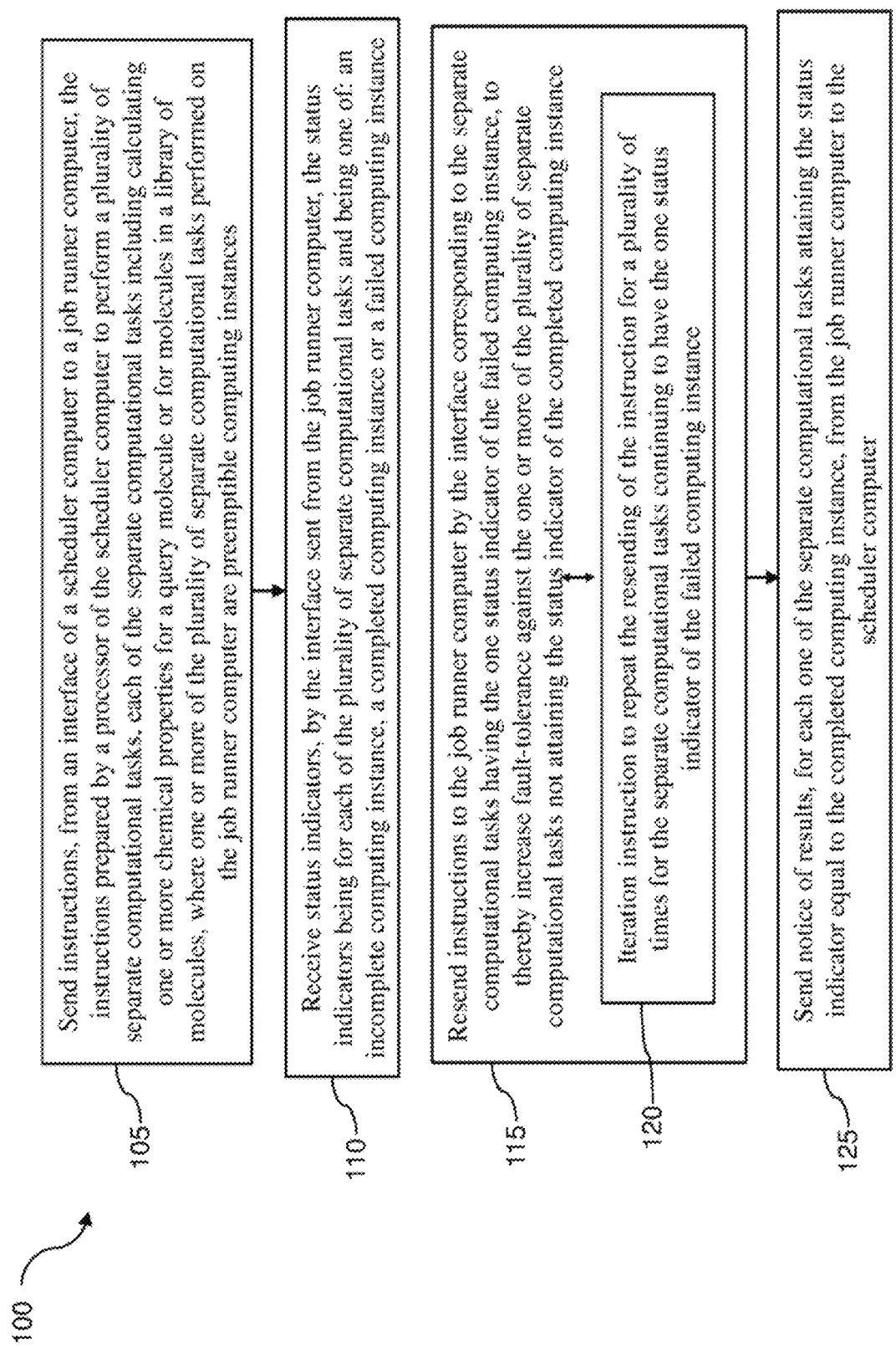
FIG. 1 illustrates a flow diagram of an example embodiment of a method of molecular scaffold hopping according to the principles of the disclosure.

FIG. 3A presents an example 2D molecular formula of an example query molecule; and FIG. 3B presents an example ensemble of 3D conformers of the example query molecules presented in FIG. 3A.

SUMMARY

In one aspect, the disclosure provides a method of molecular scaffold hopping. The method includes sending instructions, from an interface of a scheduler computer to a job runner computer, the instructions prepared by a processor of the scheduler computer, to perform a plurality of separate computational tasks, wherein each of the separate computational tasks includes calculating one or more chemical properties for a query molecule or for molecules in a library of molecules, wherein one or more of the plurality of separate computational tasks performed on the job runner computer are preemptible computing instances. The method further includes receiving status indicators, by the interface, the status indicators sent from the job runner computer, for each of the plurality of separate computational tasks, wherein each of the status indicators are one of: an incomplete computing instance, a completed computing instance or a failed computing instance. The method also includes resending to the job runner computer by the interface, the instructions to the job runner computer that correspond to the separate computational tasks having the one status indicator of the failed computing instance to thereby increase fault-tolerance against the one or more of the plurality of separate computational tasks not attaining the status indicator of the completed computing instance.

In another aspect the disclosure provides for an apparatus for molecular scaffold hopping. The apparatus includes a scheduler computer including a processor and an interface. The processor is configured to prepare instructions to perform a plurality of separate computational tasks, wherein each of the separate computational tasks includes calculating one or more chemical properties for a query molecule or for molecules in a library of molecules, wherein one or more of the plurality of separate computational tasks are preemptible computing instances. The interface is configured to send the instructions to a job runner computer, and receive from the job runner computer, a status indicator of each of the plurality of separate computational tasks, wherein the status indicator is one of an incomplete computing instance, a completed computing instance or a failed computing instance. The interface is also configured to resend to the job runner computer, the instructions that correspond to the separate computational tasks having the status indicator of the failed computing instance to thereby increase fault-tolerance against the one or more of the plurality of separate computational tasks not attaining the status indicator of the completed computing instance.

DETAILED DESCRIPTION

We disclose herein a method and apparatus for performing molecular scaffold hopping on a large scale and in a time- and cost-efficient manner by using a preemptible computing environment.

Preemptible computing refers to a non-reserved use of a plurality of computers, e.g., computing cores in a cloud computing environment, to perform a series of computational tasks, or jobs. However, some or all of the computational tasks can be pre-empted by a reserved use of the same computers to perform different computational tasks or jobs. Reserved computing refers to the reserved use of the plurality of computers for as long as needed to perform and finish a series of computational tasks before releasing the computing resource for other computational tasks.

Because the discounted fee for preemptible computing can be several times lower than the fee for reserved computing, it was desirable for our molecular scaffold hopping computations to be carried out in a preemptible computing environment instead of a reserved computing environment. However several problems had to be overcome.

One problem is that when a preemptible computational task gets preempted, e.g., by a reserved computing task, then the preemptible computational task can be 'killed', or terminated, and the task simply disappears, with no partial results being saved and no notice that the task has been killed. In some systems a signal notifying that the task will preempted in a short period (e.g., 30 s) may be given. Because no results are obtained from the preemptible computational task up to the point of being killed the entire task has to be repeated from the beginning, resulting in added time and costs. And, if multiple instances of such preemptible computational tasks are killed, then the logistical time and effort for an individual to investigate and keep track of which tasks were completed and which tasks were killed and therefore needs to be repeated, adds to the time and cost for a molecular scaffold hopping computation to be completed.

Another problem is that preemptible computational task can fail for other reasons than being pre-empted and killed by instances of reserved computing tasks. For instance, there can be a loss in communications, e.g., due to an internet failure, or other network partition, between the computers performing the computational tasks and/or a computer sending information needed perform the tasks or receiving information describing the results of completed tasks. For instance, if the computer sending information receives too many requests at about the same time then that computer can crash.

To address these problems, our idea was to increase the fault-tolerance of molecular scaffold hopping in a preemptible computing environment by developing a method and apparatus to divide the computational tasks for molecular scaffold hopping into a plurality (e.g., thousands or tens of thousands) of small preemptible computing tasks, which each take a short enough period (e.g., minutes) to complete to have a high probability of completing before failure. Another idea was for our method and apparatus to include automated computer monitoring of the status of each of the computational tasks and retry any of the computational tasks that failed to complete within a configurable number of times as further disclosed below.

One embodiment of the disclosure is a method of molecular scaffold hopping.

Figure 2:
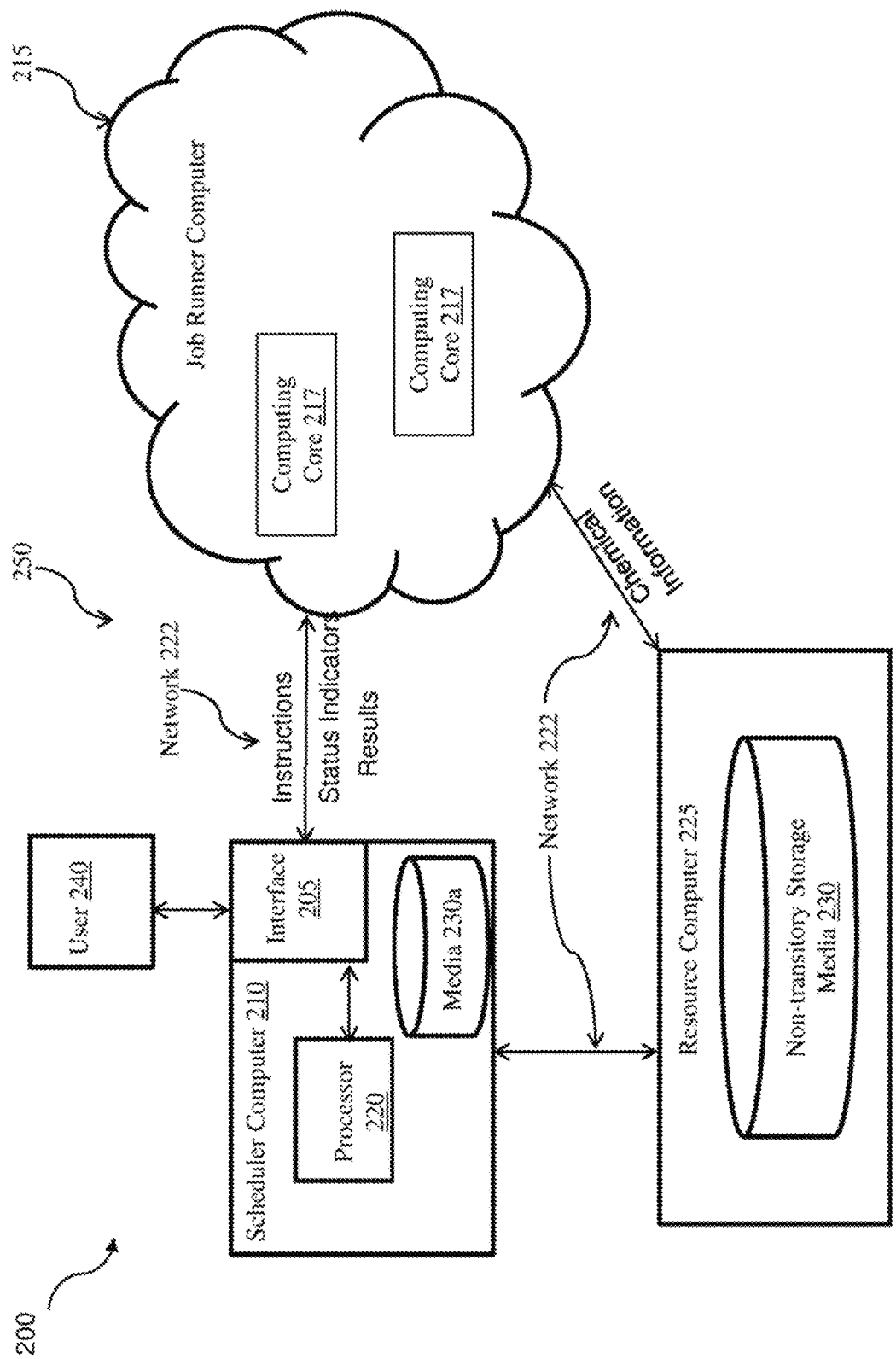
FIG. 2 illustrates a block diagram of an example apparatus embodiment of the disclosure, e.g., an apparatus to implement embodiments of the method such as disclosed in the context of FIG. 1.

FIG. 1 illustrates a flow diagram of an example embodiment of a method 100 of molecular scaffold hopping according to the principles of the disclosure. FIG. 2 illustrates a block diagram of an example apparatus 200 embodiment of the disclosure, e.g., an apparatus to implement embodiments of the method such as disclosed in the context of FIG. 1.

With continuing reference to FIGS. 1-2 throughout, as illustrated, the method 100 includes sending instructions (e.g., step 105), from an interface of a scheduler computer (e.g., interface 205 of scheduler computer 210) to a job runner computer (e.g., a job runner computer 215 having one or more computing cores 217). The instructions are prepared by a processor of the scheduler computer (e.g., processor 220), to perform a plurality of separate computational tasks, each of the separate computational tasks including calculating one or more chemical properties for a query molecule or for molecules in a library of molecules. One or more of the plurality of separate computational tasks performed on the job runner computer are preemptible computing instances.

The method 100 includes receiving status indicators, by the interface 205 sent from the job runner computer 215, (e.g., step 110). The status indicators, sent from the job runner computer, are for each of the plurality of separate computational tasks. Each of the status indicators are one of: an incomplete computing instance, a completed computing instance or a failed computing instance.

The method 100 includes resending to the job runner computer 215 by the interface 205 (e.g., step 115), the instructions to the job runner computer that correspond to the separate computational tasks having the one status indicator of the failed computing instance, to thereby increase fault-tolerance against the one or more of the plurality of separate computational tasks not attaining the status indicator of the completed computing instance.

The term separate computational task refers to the computer computation or calculation of the one or more chemical properties query molecule or set of molecules, e.g., including calculations necessary to filter sets of molecules by molecular properties, including molecular weight, enumerate stereoisomers, creating 3D conformer ensembles of the molecules, calculate 2D molecular formulas and fingerprints, indexing the set of molecules for fast searching and then for a query molecule, computing query molecule's chemical property similarity to the set of molecules as further described below.

Referring to the status indicators, a completed computing instance refers to where the job runner computer has finished calculating the one or more chemical properties and the job runner computer has stopped the computational task. An incomplete computing instance refers where the job runner computer has not finished calculating the one or more chemical properties and the job runner computer is still running the computational task. A failed computing instance refers to where there is neither an incomplete computing instance nor a completed computing instance associated with the computational task.

The term preemptible computing instances refers to any computing instance which can be replaced, at any time, by reserved computing instances operating on the job runner computer or other system event (e.g., due to system maintenance) or after a fixed time count (e.g., a 24-hour or other fixed-time counter) that is allowed on the job runner computer.

The term increase fault-tolerance refers to the ability of the disclosed method and apparatus embodiments, with no human intervention, to automatically resend the instruction to repeat any of the separate computational tasks until all of the separate computational tasks have a status indicator equal to a completed computing instance. In some instances, however, a status indicator equal to a failure can still be obtained for a separate computational task even after a configurable number and timing of resends of the task, according to step 115, e.g., (e.g., two to 100 resends over the course of several minutes of hours of timings).

The molecules in the library of molecule refer to a collection of molecules that are readily synthesizable, e.g., by a chemistry vendor, and, that are been selected for having drug-like properties (e.g., known or thought to have a physiological effect on living cells).

The term query molecule refers to a theoretical molecule, a newly synthesized molecule, or an existing molecule, which is hypothesized or known to have drug-like properties for a target disease. E.g., the query molecule can be any kind of molecule that is desired to be compared to the molecules of the library.

In some embodiments of the method, to facilitate minimizing computational resources and network communication time, the resending of the instructions (step 115) does not include the instructions corresponding to the separate computational tasks having the status indicator equal to the incomplete computing instance or equal to the complete computing instance. E.g., the instruction resent in step 115 include only the instructions corresponding to the computational task having the failed computing instance status indicator.

In some embodiments, to further increase fault tolerance, as part of step 115 the resending of the instructions further includes an iteration instruction (step 120) to repeat the resending of the instruction for a plurality of times for the separate computational tasks continuing to have the one status indicator of the failed computing instance. E.g., the scheduler computer 210 can configure the instructions sent by the interface 205 in step 115 to include a plurality of repeat instances for repeating the resending the instructions with a wait-time between each resend instruction in accordance with step 120. Thus, for such embodiments, the one computational task would have to have multiple consecutive failure status indicators spend across a period of time (e.g., 5 minutes to hours) during which the preemptible computing resources of the job runner computer are engaged. However to avoid possibility of an endless iteration loop or excessive computing resources, the number of repeat instance can be limited to a finite number (e.g., 2, 5, 10, 100 repeat instances).

In some embodiments, to minimize computing costs, all of the separate computational tasks performed on the job runner computer as instructed in step 110 are preemptible computing instances. However, in some embodiments one or more of the separate computational tasks can be designated to be performed on the job runner computer as reserved computing instances.

In some embodiments, to provide a broad range of fault tolerance, the failed computing instance can occur due to one or more of: a preemption of at least one of the separate computational tasks; a network partition between the scheduler computer and the job runner computer; a network partition between the job runner computer and a resource computer (e.g., FIG. 2, resource computer 225) that includes a digital record of chemical information (e.g., the chemical information recorded on non-transitory digital data storage media 230) about the query molecule or the molecules in the library of molecules; or an excess number of information requests from the job runner computer to a resource computer that includes a digital record of chemical information about the query molecule or the molecules in the library of molecules.

In some embodiments, to reduce the time required for each of the separate computational tasks to complete, e.g., before being preempted by a reserved computing instance, the instructions sent from the interface of the scheduler computer to the job runner computer as part of step 105 can include instructions to divide the plurality of separate computational tasks into portions divided that are completed in an average completion time that is less than an average preemption time for the one or more of the separate computational instances. The division of the tasks into portions can be specified by a user and incorporated by the processor 220 into the instructions sent to the job runner computer 215 by the interface. For instance, in some such embodiments, the portions of the plurality of separate computational tasks includes calculating the one or more chemical properties for distinct subsets of the molecules in the library of molecules. E.g., each of the distinct subsets of the molecules in the portions can be a collection ranging from $1/10000$ to $1/10$ of different ones of the molecule of a total number of the molecule in the library of molecules. E.g., in some embodiments, if the total number of the molecule in the library of molecules equals 1 billion molecules, then each of the distinctive subsets can range from 100,000 to 100,000,000 molecules.

In some embodiments, to increase fault tolerance, the instructions sent from the interface of the scheduler computer to the job runner computer as part of step 105 can include instructions to initiate performing at least two of the separate computational tasks at different times from each other. For instance, as noted elsewhere herein, one cause of a failure occurs because there are too many requests sent in a given amount of time, e.g., too many concurrent requests or nearly concurrent requests sent to an external service computer, e.g., for packets of information related to the chemical data, from the multiple job runner computer because there is too much traffic. To help prevent this the scheduler computer can control the sending out of computational tasks out to the job runner computer at slight intervals or delay times. Thus, while the separate computational tasks, once running, can run in parallel, the individual separate computational tasks can each start at different times at slightly different times than each other. E.g., in some embodiments, the scheduler computer, to help avoid overwhelming the job runner computer, can queue up the separate computational tasks and/or start or run a configurable limited number of the tasks at the same time. E.g., in some embodiments, the initiating of performing each of the separate computational tasks can be sequential in time. E.g., in some embodiments, a delay time can be set between the initiating of performing a first one of the separate computational tasks and the initiating of performing a second one of the separate computational tasks. E.g., the delay time can be set to a value (e.g., 1, 2, 5, 10, 60 seconds) that is greater than an average time for the job runner computer to access a resource computer that includes a digital record of chemical information about the query molecule or the molecules in the library of molecules.

Similarly, in some embodiments, the resending of the instructions corresponding to the separate computational task having the one status indicator equal to the failed computing instance, in accordance with step 115, can further includes instructions to initiate performing at least two of the separate computational tasks of such failed computing instances at different times from each other.

Various strategies can be adopted in the method to facilitate the efficient computing of chemical properties and thereby improve fault tolerance.

In some embodiments, the separate computational tasks to calculate the one or more chemical properties can include molecular weight filtering of the molecules in the library of molecules to select a subset library of molecules that are within a multiplier of a molecular weight of the query molecule can be adjusted to different ranges to narrow or expand the size of the subset library of molecules, e.g., the multiplier of the molecular weight of the query molecule can be in a range from $3/4$ to $5/4$ times, $1/2$ to 2 times, $1/3$ to 3 times, $1/4$ to 4 times, or other combinations thereof.

In some embodiments, the separate computational tasks to calculate the one or more chemical properties includes calculating an ensemble of 3D conformers of the query molecule or of the molecules in the library. In some such embodiments, at least 5, 7 or 10 and not more than 10, 15, or 20 3D conformers, respectively, are calculated for each of the query molecule and the molecules in the library. As a non-limiting example, FIG. 3A presents an example 2D molecular formula of an example query molecule and FIG. 3B presents an example ensemble 3D conformers of the example query molecules presented in FIG. 3A.

In some such embodiments, an energy window between any pair of 3D conformers in the ensemble of 3D conformers is less than 5 kcal. The term energy window as used herein means the difference in relative energy between a conformer and the conformer with minimum energy for a query molecule. In some embodiments, the energy window can be computed by calculating the energies of each conformer in an ensemble of conformers via Merck Molecular Force Fields, identifying the conformer with minimum relative energy (relative to the other conformers in the ensemble). In some embodiments, restricting conformer ensembles to an energy window of, e.g., 1, 2, 3, 4, 5, 6, 7, 8, 9, 10, 15 or 20 kcal helps to avoid unrealistic conformations being included in the ensemble.

In some embodiments, the separate computational tasks to calculate the one or more chemical properties includes calculations to align one of the 3D conformers of the query molecule with one of the 3D conformers of one of the molecules in the library of molecules to form an aligned conformer pair having a minimized molecular volumes difference and include calculating a Tanimoto shape similarity score representative of the minimized molecular volumes difference (e.g., a score of 0 to 1 on an arbitrary scale) as familiar to those skilled in the art. In some such embodiments, the separate computational tasks to calculate the one or more chemical properties further includes calculating an electrostatic charge difference map for the aligned conformer pairs and calculating a Tanimoto charge similarity score representative of the electrostatic charge difference map (e.g., e.g., a score of 0 to 1 on an arbitrary scale) as familiar to those skilled in the art.

In some such embodiments, the separate computational tasks to calculate the one or more chemical properties further includes adding the Tanimoto shape similarity score and the Tanimoto charge similarity score together to give a combined Tanimoto shape-electrostatic similarity score (e.g., a combined score of 0 to 2). As understood by those skilled in the art, a user can specify a threshold score for how similar a molecule has to be in order to be returned as a hit (e.g., a molecule with similar shape and electrostatic as the query molecule charge having a combined scores equal to or greater than 1.1, 1.2, 1.3, 1.4, 1.5, 1.6, 1.7, 1.8 or 1.9), or, the user can specify the maximum number of molecules to be returned with the highest scores without specifying a particular threshold score.

In some embodiments, the separate computational tasks to calculate the one or more chemical properties includes calculating a 2D molecular fingerprint difference between the query molecule and one of the molecules of the library of molecules, and, calculating a Tanimoto molecular fingerprint similarity score representative of the 2D molecular fingerprint difference (e.g., a score of 0 to 1 on an arbitrary scale) as familiar to those skilled in the art. One skilled in the pertinent art would be familiar with the calculation of molecular fingerprints, e.g., to make a vector, or other mathematical object, representation of a molecular structure to facilitate numerically encoding structural information about the molecular structure. In some such embodiments, to help ensure that the molecules selected from the molecules of the library have different chemical core structures from that of the query molecule, the user may specify that the Tanimoto molecular fingerprint similarity score be low (e.g., 0.1 or less, 0.2 or less, 0.3 or less, 0.4 or less or 0.5 or less).

In some embodiments, the selection criterion for finding suitable molecular scaffold hopping candidates might be those molecules from the library of molecules where the combined Tanimoto shape-electrostatic similarity score is high (e.g., equal to or greater than 1.5) and the Tanimoto molecular fingerprint similarity score is low (e.g., equal to or less than 0.2). Thus, the dual filters of Tanimoto shape-electrostatic similarity score and Tanimoto molecular fingerprint similarity score facilitate identifying molecules with conformer and charge similarity but highly different chemical structural compositions than the query molecule.

As illustrated in FIG. 1, the method 100 can further includes for each one of the separate computational tasks attaining the status indicator equal to the completed computing instance, sending from the job runner computer to the scheduler computer, notice of results of the separate computational task (step 125). For instance, the notice of results of the tasks could include a listing of the molecules from the library of molecules having a suitable Tanimoto shape-electrostatic similarity score and Tanimoto molecular fingerprint similarity score as compared to the query molecule. In some embodiments, the instructions (step 105) sent to the job runner computer include instructions on where to send the results of the completed computing instance (e.g., to the scheduler computer 210, a resource computer 225 or other computer).

Another embodiment is an apparatus for molecular scaffold hopping, e.g., to implement any of the embodiments of the method. Again with continuing reference to FIGS. 1-2 throughout, embodiments of the apparatus 200 include a scheduler computer 210, the scheduler computer including a processor 220 and an interface 205. The processor can be configured to prepare instructions to perform a plurality of separate computational tasks. Each of the separate computational tasks includes calculating one or more chemical properties for a query molecule or for molecules in a library of molecules, where one or more, or sometimes all, of the plurality of separate computational tasks can be preemptible computing instances. The interface can be configured to: send the instructions to a job runner computer: receive, from the job runner computer, a status indicator of each of the plurality of separate computational tasks (one of an incomplete computing instance, a completed computing instance or a failed computing instance); and resend to the job runner computer, the instructions that correspond to the separate computational tasks having the status indicator of the failed computing instance, thereby increasing fault-tolerance against the one or more of the plurality of separate computational tasks not attaining the status indicator of the completed computing instance.

In some embodiments, the scheduler computer processor 220 can receive a request (e.g., from a user or automated user) to run the separate computational tasks to calculate the one or more chemical properties for a query molecule or for molecules in a library of molecules. The scheduler computer sends instructions (step 105) via the interface 205 to start the tasks running on job runner computer 215. In some embodiments, each of the separate computational tasks can be assigned to different computing cores 217 of the job runner computer 215. In some embodiments, upon receiving the instructions, each of the computing cores 217, can poll the scheduler computer 220 for its assigned separate computational tasks and when there are no more tasks then each computing core 217 can terminate itself.

In some embodiments, the apparatus can be part of a computing system (e.g., system 250) that also includes the job runner computer.

In some embodiments, the instructions prepared by the processor and sent by the interface can include an iteration instruction to repeat the resending of the instruction for a plurality of times for the separate computational tasks continuing to have the one status indicator of the failed computing instance.

In some embodiments, the processor can be configured (e.g., via a digital programming language) to prepare the instructions based on dividing the plurality of separate computational tasks into portions that are completed in an average completion time that is less than an average preemption time for the one or more of the separate computational instances.

In some embodiments, the instructions prepared by the processor and sent by the interface include instructions initiate performing at least two of the separate computational tasks at different times from each other.

In some embodiments, the instructions prepared by the processor and sent by the interface include instructions for the resending of the instructions, corresponding to the separate computational task having the status indicator equal to the failed computing instance, include further instructions to initiate performing at least two of the separate computational tasks at different times from each other.

In some embodiments, at least one the separate computational tasks to calculate the one or more chemical properties includes molecular weight filtering of the molecules in the library of molecules to select a subset library of molecules that are within a multiplier of a molecular weight of the query molecule. In some embodiments, at least one of the separate computational tasks to calculate the one or more chemical properties includes calculating an ensemble of 3D conformers of the query molecule or of the molecules in the library. In some embodiments, at least one the separate computational tasks to calculate the one or more chemical properties includes calculations to align one of the 3D conformers of the query molecule with one of the 3D conformers of one of the molecules in the library of molecules to form an aligned conformer pair having a minimized molecular volumes difference and calculating a Tanimoto shape similarity score representative of the minimized molecular volumes difference. In some embodiments, at least one of the separate computational tasks to calculate the one or more chemical properties includes calculating a 2D molecular fingerprint difference between the query molecule and one of the molecules of the library of molecules, and, calculating a Tanimoto molecular fingerprint similarity score representative of the 2D molecular fingerprint difference.

In some embodiments, the instructions prepared by the processor and sent by the interface include instructions for the job runner computer to send results of the separate computational tasks to the interface, for each one of the separate computational tasks that attains the status indicator equal to the completed computing instance.

Some embodiments of the apparatus 100 include a resource computer 225 configured to store chemical information about the library of molecules or query molecule in non-transitory storage media 230 and provide such information when requested by the job runner computer 215 or computing cores of the job runner computer. In some embodiments, the resource computer 225 or non-transitory storage media 230 can be part of the scheduler computer 210. In other embodiments, the scheduler computer 210 can have separate non-transitory storage media 230a, e.g., used for keeping track of the separate computational, tasks such as which of the tasks are waiting to run, running, failed or completed. The job runner computer 215 or its computing cores 217 can include separate storage media to store input data obtained from the resource computer 225 and output data.

The interface 205 includes the necessary circuitry, components, firmware, software, etc., to transmit and receive data as an input/output interface. The interface 205 can be a conventional interface associated with the processor 220 to communicate data according to different standard protocols, such as industry or proprietary protocols used for communicating data between computing devices. The interface 205 can be configured to communicate via a communications network (e.g., network 222) when remotely located from the job runner computer 215, such as when the job runner computer is cloud-based. The communications network 222 can be a conventional communications network that communicates via standard protocols.

In some embodiments, the job runner computer 215 can be or include a single computer with one or more computing cores 217 (e.g., a plurality of GPUs and/or CPUs) or each of the computing cores 217. In some embodiments, the job runner computer 215 can include one or more individual computers configured as virtual machines or computing clusters located proximate each other, or in a cloud environment, in a data center, or a combination thereof.

The processor 220 can be configured to control the operation of the scheduler computer 210 and interface 205. The processor 220, for example, can include the necessary logic circuitry embodied in digital data processors such as CPU or GPUs, to store executable programs or software instruction and to send and receive digital information to and from the interface 205.

In some embodiments, a user 240 (e.g., a human or automated process) can interact with the scheduler computer 210 via the interface 205, by submitting or monitoring the separate computational tasks.

Those skilled in the art to which this application relates will appreciate that other and further additions, deletions, substitutions and modifications may be made to the described embodiments.

What is claimed:

1. A method of molecular scaffold hopping, comprising:
sending instructions, from an interface of a scheduler computer to a job runner computer, the instructions prepared by a processor of the scheduler computer, to perform a plurality of separate computational tasks, wherein each of the separate computational tasks includes calculating one or more chemical properties for a query molecule or for molecules in a library of molecules, wherein one or more of the plurality of separate computational tasks performed on the job runner computer are preemptible computing instances, wherein the instructions sent from the interface of the scheduler computer to the job runner computer include instructions to set a delay time between initiation of performing a first one of the separate computational tasks and initiation of performing a second one of the separate computational tasks, wherein the delay time is related to an average time for the job runner computer to access a resource computer that includes a digital record of chemical information about one of the query molecule and the molecules of the library of molecules;
receiving status indicators, by the interface, the status indicators sent from the job runner computer, for each of the plurality of separate computational tasks, wherein each of the status indicators are one of: an incomplete computing instance, a completed computing instance, or a failed computing instance; and
resending to the job runner computer by the interface, the instructions to the job runner computer that correspond to the separate computational tasks having the status indicator of the failed computing instance to thereby increase fault-tolerance against the one or more of the plurality of separate computational tasks not attaining the status indicator of the completed computing instance.

2. The method of claim 1, wherein the resending of the instructions does not include the instructions corresponding to the separate computational tasks having the status indicator equal to the incomplete computing instance or equal to the complete computing instance.

3. The method of claim 1, wherein the resending of the instructions further includes an iteration instruction to repeat the resending of the instruction for a plurality of times for the separate computational tasks continuing to have the status indicator of the failed computing instance.

4. The method of claim 1, wherein all of the separate computational tasks performed on the job runner computer are preemptible computing instances.

5. The method of claim 1, wherein all of the preemptible computing instances may be replaced at any time by one of a reserved computing instance operating on the job runner computer, another system event on the job runner computer, and expiration of a fixed-time counter on the job runner computer.

6. The method of claim 1, wherein the failed computing instance occurs due to one or more of:
- a preemption of at least one of the separate computational tasks;
- a network partition between the scheduler computer and the job runner computer;
- a network partition between the job runner computer and a resource computer that includes a digital record of chemical information about the query molecule or the molecules in the library of molecules; or
- an excess number of information requests from the job runner computer to a resource computer that includes a digital record of chemical information about the query molecule or the molecules in the library of molecules.

7. The method of claim 1, wherein the instructions sent from the interface of the scheduler computer to the job runner computer include instructions to initiate performing at least two of the separate computational tasks at different times from each other.

8. The method of claim 1, wherein the separate computational tasks to calculate the one or more chemical properties includes molecular weight filtering of the molecules in the library of molecules to select a subset library of molecules that are within a multiplier of a molecular weight of the query molecule.

9. The method of claim 1, wherein the separate computational tasks to calculate the one or more chemical properties includes:
- calculating an ensemble of 3D conformers of the query molecule and the molecules in the library of molecules;
- calculating an energy window by computing the energies of each 3D conformer in each ensemble of 3D conforms via Merck Molecular Force Fields; and
- identifying, in each ensemble, the 3D conformer with the minimum energy relative to other 3D conformers of its respective ensemble.

10. An apparatus for molecular scaffold hopping, the apparatus comprising:
- a scheduler computer, the scheduler computer including a processor and an interface, wherein:
  - the processor is configured to prepare instructions to perform a plurality of separate computational tasks, wherein each of the separate computational tasks includes calculating one or more chemical properties for a query molecule or for molecules in a library of molecules, wherein one or more of the plurality of separate computational tasks are preemptible computing instances; and
  - the interface is configured to:
    - send the instructions to a job runner computer, wherein the instructions sent from the interface of the scheduler computer to the job runner computer include instructions to set a delay time between initiation of performing a first one of the separate computational tasks and initiation of performing a second one of the separate computational tasks, wherein the delay time is related to an average time for the job runner computer to access a resource computer that includes a digital record of chemical information about one of the query molecule and the molecules of the library of molecules;
    - receive from the job runner computer, a status indicator of each of the plurality of separate computational tasks, wherein the status indicator is one of: an incomplete computing instance, a completed computing instance, or a failed computing instance, and
    - resend to the job runner computer, the instructions that correspond to the separate computational tasks having the status indicator of the failed computing instance to thereby increase fault-tolerance against the one or more of the plurality of separate computational tasks not attaining the status indicator of the completed computing instance.

11. The apparatus of claim 10, further comprising:
a resource computer configured to:
- store chemical information about at least one of the library of molecules and the query molecule; and
- provide the stored chemical information to the job runner computer upon request by the job runner computer.

12. The apparatus of claim 10, wherein the scheduling computer further comprises a non-transitory storage media configured for tracking the separate computational tasks and their respective states, wherein the states are selected from: waiting to run, running, failed, and completed.

13. The apparatus of claim 10, wherein the apparatus is part of a computing system that also includes the job runner computer.

14. The apparatus of claim 10, wherein the instructions prepared by the processor and sent by the interface includes an iteration instruction to repeat the resending of the instruction for a plurality of times for the separate computational tasks continuing to have the status indicator of the failed computing instance.

15. The apparatus of claim 10, wherein the instructions prepared by the processor and sent by the interface include instructions initiate performing at least two of the separate computational tasks at different times from each other.

16. The apparatus of claim 10, wherein at least one the separate computational tasks to calculate the one or more chemical properties includes molecular weight filtering of the molecules in the library of molecules to select a subset library of molecules that are within a multiplier of a molecular weight of the query molecule.

17. The apparatus of claim 10, the instructions prepared by the processor and sent by the interface includes instructions to set a delay time between initiation of performing a first one of the separate computational tasks and initiation of performing a second one of the separate computational tasks, wherein the delay time is related to an average time for the job runner computer to access a resource computer that includes a digital record of chemical information about one of the query molecule and the molecules of the library of molecules.

18. The apparatus of claim 10, wherein the separate computational tasks to calculate the one or more chemical properties includes:
   calculation of an ensemble of 3D conformers of the query molecule and the molecules in the library of molecules;
   calculation of an energy window by computing the energies of each 3D conformer in each ensemble of 3D conforms via Merck Molecular Force Fields; and
   identification, in each ensemble, of the 3D conformer with the minimum energy relative to other 3D conformers of its respective ensemble.

19. A non-transitory computer-readable storage media comprising instructions stored thereon which, when executed, cause a computer system to perform a method of molecular scaffold hopping, the method comprising:
   sending instructions, from an interface of a scheduler computer to a job runner computer, the instructions prepared by a processor of the scheduler computer, to perform a plurality of separate computational tasks, wherein each of the separate computational tasks includes calculating one or more chemical properties for a query molecule or for molecules in a library of molecules, wherein one or more of the plurality of separate computational tasks performed on the job runner computer are preemptible computing instances, wherein the instructions sent from the interface of the scheduler computer to the job runner computer include instructions to set a delay time between initiation of performing a first one of the separate computational tasks and initiation of performing a second one of the separate computational tasks, wherein the delay time is related to an average time for the job runner computer to access a resource computer that includes a digital record of chemical information about one of the query molecule and the molecules of the library of molecules;
   receiving status indicators, by the interface, the status indicators sent from the job runner computer, for each of the plurality of separate computational tasks, wherein each of the status indicators are one of: an incomplete computing instance, a completed computing instance, or a failed computing instance; and
   resending to the job runner computer by the interface, the instructions to the job runner computer that correspond to the separate computational tasks having the status indicator of the failed computing instance to thereby increase fault-tolerance against the one or more of the plurality of separate computational tasks not attaining the status indicator of the completed computing instance.

* * * * *